(12) United States Patent
Windisch et al.

(10) Patent No.: US 7,785,830 B2
(45) Date of Patent: Aug. 31, 2010

(54) EXPRESSION VECTORS, TRANSFORMED HOST CELLS AND FERMENTATION PROCESS FOR THE PRODUCTION OF RECOMBINANT POLYPEPTIDES

(75) Inventors: Jörg Windisch, Kramsach (AT); Kurt Schoergendorfer, Langkampfen (AT); Norbert Palma, Breitenbach a. Inn (AT); Franz Knauseder, Kirchbichl (AT); Hans Boehling, Kufstein (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/568,337

(22) PCT Filed: Aug. 12, 2004

(86) PCT No.: PCT/EP2004/009067

§ 371 (c)(1),
(2), (4) Date: Apr. 12, 2006

(87) PCT Pub. No.: WO2005/017162

PCT Pub. Date: Feb. 24, 2005

(65) Prior Publication Data

US 2006/0228783 A1  Oct. 12, 2006

Related U.S. Application Data

(60) Provisional application No. 60/494,914, filed on Aug. 13, 2003.

(51) Int. Cl.
*C12N 1/19*  (2006.01)
*C12P 21/06*  (2006.01)
*C12N 15/11*  (2006.01)

(52) U.S. Cl. ............... 435/69.1; 435/252.3; 435/252.34; 435/320.1; 536/23.1; 536/23.4; 536/23.7

(58) Field of Classification Search ................. None
See application file for complete search history.

(56) References Cited

U.S. PATENT DOCUMENTS

| | | | |
|---|---|---|---|
| 4,680,262 | A | 7/1987 | Bochner et al. |
| 5,648,237 | A | 7/1997 | Carter |
| 5,710,027 | A | 1/1998 | Hauptmann et al. |
| 2003/0026805 | A1 | 2/2003 | Athwal et al. |
| 2004/0151695 | A1 | 8/2004 | Kwon et al. |

FOREIGN PATENT DOCUMENTS

| | | |
|---|---|---|
| EP | 0 974 654 | 1/2000 |
| WO | WO 89/00201 | 1/1989 |
| WO | WO 01/57217 | 8/2001 |
| WO | WO 03/004599 | 1/2003 |

OTHER PUBLICATIONS

Kim et al., 2001 Cloning and high expression of glutaryl 7-aminocephalosporanic acid acylase gene from Pseudomonas diminuta. Biobechnology Letters pp. 1067-1071.*

Ishii et al., 1994 A Novel 7-β-(4-Carboxybutanamido)-Cephalosporanic Acid Acylase Isolated from Pseudomonas Strain C427 and Its High-Level Production in *Escherichia coli*. Journal of fermentation and bioengineering, pp. 591-597.*

Bourdineaud J P et al: "Cytoplasmic and Periplasmic Expression of a Synthetic gene for Ferredoxin in *Escherichia-coli*", Biochimie (Paris), vil.72, No. 6-7, 1990, pp. 407-415, XP002316190.

Weickert M J et al: "Optimization of Heterologous Protein Production in *Escherichia coli*", Current opinion in Biotechnology. London, GB, vol. 7, No. 5, 1996, pp. 494-499, XP000995157.

Humphreys D P et al:"High-Level Periplasmic Expression in *Escherichia coli* Using a Eukaryotic Signal Peptide: Importance of Codon usage at the 5' end of the coding sequence" Protein expression and purification academic press, San Diego, CA, US, vol. 20, No. 2, Nov. 2000, pgs.

Matsuda A et al:"Molecular Cloning and Structure of the Gene for 7-beta-4 Carboxybutanamidocephalosporanic-acid acylase from a pseudomonas strain", Journal of Bateriology, vol. 163, No. 3, 1985, pp. 1222-1228, XP002316191.

French C et al:"Development of a simple method for the recovery of recombinant proteins from the *Escherichia coli* periplasm" Enzyme and Microbial Technology, Stoneham, MA, US, vol. 19, No. 5, 1996, pp. 332-338, XP000886796.

Dalmora S et al: "Analysis of recombinant human growth hormone directly in osmotic shick fluids" Journal of Chromatography A, Elsevier Science, NL., vols. 782, No. 2, Oct. 10, 1997, pp. 199-210, XP004096275.

Anderson D C et al: "Production technologies for monoclonal antibodies and their fragments", Current opinion in Biotechnology, vol. 15, No. 5, Oct. 2004, pp. 456-462.

De Oliveira J E et al: "High-yeild purification of biosynthetic human growth hormone secreted in *Escherichia coli* periplasmic space" Journal of Chromatogrpahy A, Elsevier Science, NL. vol. 852, No. 2 Aug. 13, 1999, pp. 441-450.

Hannig G et al:"Strategies for optimizing heterologous protein expression in *Escherichia coli*", Trends in Biotechnology, vol. 16, No. 2., Feb. 1998, pp. 54-60, XP004107042.

Middleberg A P J: "Process-scale disruption of microorganisms" Biotechnology Advances, vol. 13, No. 3 1995, pp. 491-551, XP004045404.

Baneyx F: Recombinant protein expression in *Escherichia coli* current opinion in Biotechnology, vol. 10, No. 5, Oct. 1999, pp. 411-421, XP001041299.

Hart R A et al: "Large scale, in situ isolation of periplasmic IGF-I from *E. Coli*", Bio Technology, vol. 12, Nov. 1994, pp. 1113-1117, XP001153305.

* cited by examiner

*Primary Examiner*—Maria Leavitt
(74) *Attorney, Agent, or Firm*—Luedeka, Neely & Graham, P.C.

(57) ABSTRACT

The present invention relates to an expression vector, comprising a polynucleotide encoding a fusion protein comprising the signal sequence of the gac gene of *Pseudomonas diminuta* and a polypeptide of interest, a prokaryotic host cell transformed with such an expression vector and a process for production of a polypeptide of interest using said host cell and said expression vector.

39 Claims, No Drawings

SEQUENCE LISTING

```
<160> NUMBER OF SEQ ID NOS: 19

<210> SEQ ID NO 1
<211> LENGTH: 495
<212> TYPE: DNA
<213> ORGANISM: Artificial
<220> FEATURE:
<223> OTHER INFORMATION: DNA encoding human interferon alpha 2B with
      altered codon usage

<400> SEQUENCE: 1
tgcgatctgc cgcaaaccca cagcctgggt agccggcgaa ccttgatgct tctggcacag     60
atgcggcgaa tctctctttt ctcttgctta aaggatcgac atgacttcgg tttcccgcag    120
```

```
gaggagttcg gtaaccagtt ccaaaaggct gaaaccatcc cggtattgca tgagatgatc      180
cagcagatct tcaacctgtt cagcactaag gactcttctg ctgcttggga tgagaccctg      240
cttgacaaat tctacactga actgtaccag cagctgaacg acctggaagc ctgcgtgatc      300
cagggtgtgg gtgtgactga gactccgctg atgaaggagg actctattct ggctgtgcga      360
aaatacttcc aacggatcac tctgtatctg aaagagaaga aatacagccc gtgcgcctgg      420
gaggttgtcc gagcagaaat catgcggtct ttctcttttgt ctaccaactt gcaagaatct      480
ttacgaagca aggaa                                                      495
```

<210> SEQ ID NO 2
<211> LENGTH: 27
<212> TYPE: PRT
<213> ORGANISM: Pseudomonas diminuta

<400> SEQUENCE: 2

Met Leu Arg Val Leu His Arg Ala Ala Ser Ala Leu Val Met Ala Thr
1               5                   10                  15

Val Ile Gly Leu Ala Pro Ala Val Ala Phe Ala
            20                  25

<210> SEQ ID NO 3
<211> LENGTH: 81
<212> TYPE: DNA
<213> ORGANISM: Pseudomonas diminuta

<400> SEQUENCE: 3

```
atgctgagag ttctgcaccg ggcggcgtcc gccttggtta tggcgactgt gatcggcctt      60
gcgcccgccg tcgcctttgc g                                                81
```

<210> SEQ ID NO 4
<211> LENGTH: 81
<212> TYPE: DNA
<213> ORGANISM: Artificial
<220> FEATURE:
<223> OTHER INFORMATION: DNA encoding signal sequence of gac gene of
      Pseudomonas diminuta with altered codon usage

<400> SEQUENCE: 4

```
atgctgagag ttctgcaccg ggcggcgtcc gccttggtta tggcgactgt gatcggcctt      60
gcgcccgcgg tcgcctttgc g                                                81
```

<210> SEQ ID NO 5
<211> LENGTH: 100
<212> TYPE: DNA
<213> ORGANISM: Pseudomonas diminuta

<400> SEQUENCE: 5

```
atcctggttc gtacgcgccg cctacaagtg gtgatctagg gaacgttccg ggggcgtcg       60 ctgcaacggc gtctccggat ctgggtgaga ggggaaatcc                           100
```

<210> SEQ ID NO 6
<211> LENGTH: 209
<212> TYPE: DNA
<213> ORGANISM: Pseudomonas diminuta

<400> SEQUENCE: 6

```
tctagaccaa caacatcttc aacgtctacc cgaccaagat tcaggagccg tcggccgacc      60
tgggcaatgg gatgtacagc gggcttgcgc cgttcggctt caccggcgga tcctggttcg     120
```

```
tacgcgccgc ctacaagtgg tgatctaggg gaacgttccg ggggcgtcgc tgcaacggcg        180
tctccggatc tgggtgagag gggaaatcc                                         209

<210> SEQ ID NO 7
<211> LENGTH: 23
<212> TYPE: DNA
<213> ORGANISM: Artificial
<220> FEATURE:
<223> OTHER INFORMATION: Oligonucleotide, PCR primer

<400> SEQUENCE: 7
taactgtcag accaagttta ctc                                               23

<210> SEQ ID NO 8
<211> LENGTH: 20
<212> TYPE: DNA
<213> ORGANISM: Artificial
<220> FEATURE:
<223> OTHER INFORMATION: Oligonucleotide, PCR primer

<400> SEQUENCE: 8
gcgtttcggt gatgacggtg                                                   20

<210> SEQ ID NO 9
<211> LENGTH: 23
<212> TYPE: DNA
<213> ORGANISM: Artificial
<220> FEATURE:
<223> OTHER INFORMATION: Oligonucleotide, PCR primer

<400> SEQUENCE: 9
tcatgtttga cagcttatca tcg                                               23

<210> SEQ ID NO 10
<211> LENGTH: 19
<212> TYPE: DNA
<213> ORGANISM: Artificial
<220> FEATURE:
<223> OTHER INFORMATION: Oligonucleotide, PCR primer

<400> SEQUENCE: 10
ggtcgaggtg gcccggctc                                                    19

<210> SEQ ID NO 11
<211> LENGTH: 36
<212> TYPE: DNA
<213> ORGANISM: Artificial
<220> FEATURE:
<223> OTHER INFORMATION: Oligonucleotide, PCR primer

<400> SEQUENCE: 11 gggggggtcta gaccaacaac atcttcaacg tctacc                                36

<210> SEQ ID NO 12
<211> LENGTH: 32
<212> TYPE: DNA
<213> ORGANISM: Artificial
<220> FEATURE:
<223> OTHER INFORMATION: Oligonucleotide, PCR primer

<400> SEQUENCE: 12 cccccccgaat tcactagtac gcgtctctct cc                                    32

<210> SEQ ID NO 13
<211> LENGTH: 315
```

```
<212> TYPE: DNA
<213> ORGANISM: Artificial
<220> FEATURE:
<223> OTHER INFORMATION: DNA comprising part of gac gene of Pseudomonas
      diminuta

<400> SEQUENCE: 13 gggggtcta gaccaacaac atcttcaacg tctacccgac caagattcag gagccgtcgg        60
ccgacctggg caatgggatg tacagcgggc ttgcgccgtt cggcttcacc ggcggatcct     120
ggttcgtacg cgccgcctac aagtggtgat ctaggggaac gttccggggg cgtcgctgca     180
acggcgtctc cggatctggg tgagagggga aatccatgct gagagtttctg caccgggcgg    240 cgtccgcctt ggttatggcg actgtgatcg gccttgcgcc cgcggagaga gacgcgtact     300
agtgaattcg ggggg                                                      315

<210> SEQ ID NO 14
<211> LENGTH: 11
<212> TYPE: DNA
<213> ORGANISM: Artificial
<220> FEATURE:
<223> OTHER INFORMATION: Oligonucleotide, part of PCR primer

<400> SEQUENCE: 14
tcgcctttgc g                                                           11

<210> SEQ ID NO 15
<211> LENGTH: 23
<212> TYPE: DNA
<213> ORGANISM: Artificial
<220> FEATURE:
<223> OTHER INFORMATION: Oligonucleotide, PCR primer

<400> SEQUENCE: 15
ttgcgcccgc ggtcgccttt gcg                                              23

<210> SEQ ID NO 16
<211> LENGTH: 4
<212> TYPE: PRT
<213> ORGANISM: Pseudomonas diminuta

<400> SEQUENCE: 16

Val Ala Phe Ala
1

<210> SEQ ID NO 17
<211> LENGTH: 540
<212> TYPE: DNA
<213> ORGANISM: Artificial
<220> FEATURE:
<223> OTHER INFORMATION: DNA comprising nucleotide sequence encoding
      human interferon alpha 2B

<400> SEQUENCE: 17 gggggccgc ggtcgccttt gcgtgcgatc tgccgcaaac ccacagcctg ggtagccggc        60
gaaccttgat gcttctggca cagatgcggc gaatctctct tttctcttgc ttaaaggatc     120
gacatgactt cggtttcccg caggaggagt tcggtaacca gttccaaaag gctgaaacca     180
tcccggtatt gcatgagatg atccagcaga tcttcaacct gttcagcact aaggactctt     240
ctgctgcttg ggatgagacc ctgcttgaca aattctacac tgaactgtac cagcagctga     300
acgacctgga agcctgcgtg atccaggtg tgggtgtgac tgagactccg ctgatgaagg      360
aggactctat tctggctgtg cgaaaatact tccaacggat cactctgtat ctgaaagaga     420
```
agaaatacag cccgtgcgcc tgggaggttg tccgagcaga aatcatgcgg tctttctctt 480
tgtctaccaa cttgcaagaa tctttacgaa gcaaggaata atacgcgtga attcgggggg 540

<210> SEQ ID NO 18
<211> LENGTH: 807
<212> TYPE: DNA
<213> ORGANISM: Artificial
<220> FEATURE:
<223> OTHER INFORMATION: DNA encoding fusion protein comprising signal
      sequence of gac gene of Pseudomonas diminuta and human interferon
      alpha 2B
<220> FEATURE:
<221> NAME/KEY: CDS
<222> LOCATION: (210)..(788)

<400> SEQUENCE: 18
tctagaccaa caacatcttc aacgtctacc cgaccaagat tcaggagccg tcggccgacc 60
tgggcaatgg gatgtacagc gggcttgcgc cgttcggctt caccggcgga tcctggttcg 120
tacgcgccgc ctacaagtgg tgatctaggg gaacgttccg ggggcgtcgc tgcaacggcg 180
tctccggatc tgggtgagag gggaaatcc atg ctg aga gtt ctg cac cgg gcg    233
                                  Met Leu Arg Val Leu His Arg Ala
                                   1               5 gcg tcc gcc ttg gtt atg gcg act gtg atc ggc ctt gcg ccc gcg gtc    281
Ala Ser Ala Leu Val Met Ala Thr Val Ile Gly Leu Ala Pro Ala Val
 10              15                  20 gcc ttt gcg tgc gat ctg ccg caa acc cac agc ctg ggt agc cgg cga    329
Ala Phe Ala Cys Asp Leu Pro Gln Thr His Ser Leu Gly Ser Arg Arg
 25              30                  35                  40 acc ttg atg ctt ctg gca cag atg cgg cga atc tct ctt ttc tct tgc    377
Thr Leu Met Leu Leu Ala Gln Met Arg Arg Ile Ser Leu Phe Ser Cys
                 45                  50                  55 tta aag gat cga cat gac ttc ggt ttc ccg cag gag gag ttc ggt aac    425
Leu Lys Asp Arg His Asp Phe Gly Phe Pro Gln Glu Glu Phe Gly Asn
             60                  65                  70 cag ttc caa aag gct gaa acc atc ccg gta ttg cat gag atg atc cag    473
Gln Phe Gln Lys Ala Glu Thr Ile Pro Val Leu His Glu Met Ile Gln
         75                  80                  85 cag atc ttc aac ctg ttc agc act aag gac tct tct gct gct tgg gat    521
Gln Ile Phe Asn Leu Phe Ser Thr Lys Asp Ser Ser Ala Ala Trp Asp
     90                  95                 100 gag acc ctg ctt gac aaa ttc tac act gaa ctg tac cag cag ctg aac    569
Glu Thr Leu Leu Asp Lys Phe Tyr Thr Glu Leu Tyr Gln Gln Leu Asn
105                 110                 115                 120 gac ctg gaa gcc tgc gtg atc cag ggt gtg ggt gtg act gag act ccg    617
Asp Leu Glu Ala Cys Val Ile Gln Gly Val Gly Val Thr Glu Thr Pro
                125                 130                 135 ctg atg aag gag gac tct att ctg gct gtg cga aaa tac ttc caa cgg    665
Leu Met Lys Glu Asp Ser Ile Leu Ala Val Arg Lys Tyr Phe Gln Arg
            140                 145                 150 atc act ctg tat ctg aaa gag aag aaa tac agc ccg tgc gcc tgg gag    713
Ile Thr Leu Tyr Leu Lys Glu Lys Lys Tyr Ser Pro Cys Ala Trp Glu
        155                 160                 165 gtt gtc cga gca gaa atc atg cgg tct ttc tct ttg tct acc aac ttg    761
Val Val Arg Ala Glu Ile Met Arg Ser Phe Ser Leu Ser Thr Asn Leu
    170                 175                 180 caa gaa tct tta cga agc aag gaa taa tacgcgtact agtgaattc          807
Gln Glu Ser Leu Arg Ser Lys Glu
185                 190

```
<210> SEQ ID NO 19
<211> LENGTH: 192
<212> TYPE: PRT
<213> ORGANISM: Artificial
<220> FEATURE:
<223> OTHER INFORMATION: Synthetic Construct

<400> SEQUENCE: 19

Met Leu Arg Val Leu His Arg Ala Ala Ser Ala Leu Val Met Ala Thr
1               5                   10                  15

Val Ile Gly Leu Ala Pro Ala Val Ala Phe Ala Cys Asp Leu Pro Gln
                20                  25                  30

Thr His Ser Leu Gly Ser Arg Arg Thr Leu Met Leu Leu Ala Gln Met
            35                  40                  45

Arg Arg Ile Ser Leu Phe Ser Cys Leu Lys Asp Arg His Asp Phe Gly
    50                  55                  60

Phe Pro Gln Glu Glu Phe Gly Asn Gln Phe Gln Lys Ala Glu Thr Ile
65                  70                  75                  80

Pro Val Leu His Glu Met Ile Gln Gln Ile Phe Asn Leu Phe Ser Thr
                85                  90                  95

Lys Asp Ser Ser Ala Ala Trp Asp Glu Thr Leu Leu Asp Lys Phe Tyr
            100                 105                 110

Thr Glu Leu Tyr Gln Gln Leu Asn Asp Leu Glu Ala Cys Val Ile Gln
            115                 120                 125

Gly Val Gly Val Thr Glu Thr Pro Leu Met Lys Glu Asp Ser Ile Leu
        130                 135                 140

Ala Val Arg Lys Tyr Phe Gln Arg Ile Thr Leu Tyr Leu Lys Glu Lys
145                 150                 155                 160

Lys Tyr Ser Pro Cys Ala Trp Glu Val Val Arg Ala Glu Ile Met Arg
                165                 170                 175

Ser Phe Ser Leu Ser Thr Asn Leu Gln Glu Ser Leu Arg Ser Lys Glu
            180                 185                 190
```

EXPRESSION VECTORS, TRANSFORMED HOST CELLS AND FERMENTATION PROCESS FOR THE PRODUCTION OF RECOMBINANT POLYPEPTIDES

This application is a national stage application of copending PCT International Application No. PCT/EP2004/009067, filed Aug. 12, 2004. This application also claims the benefit of the filing date of U.S. provisional patent application No. 60/494,914, filed Aug. 13, 2003.

The present invention relates to an expression vector, comprising a polynucleotide encoding a fusion protein comprising the signal sequence of the gac gene of *Pseudomonas diminuta* and a polypeptide of interest, a prokaryotic host cell transformed with such an expression vector and a process for production of a polypeptide of interest using said host cell and said expression vector.

It is a subject of the present invention to provide a process for the efficient and direct production of a mature recombinant polypeptide in a prokaryotic host cell. The process according to the present invention can, for example, favourably be used for the production of recombinant human Interferon alpha 2B (rhIFNα2B) in *Escherichia coli* (*E. coli*).

In the production of recombinant proteins in prokaryotic microorganisms such as the expression of human or other eukaryotic proteins in bacterial cells it is often difficult to obtain a clearly defined N-terminus which is as nearly 100% homogeneous as possible. This applies in particular to recombinant pharmaceutical proteins whose amino acid sequence ought in many cases to be identical to the amino acid sequence naturally occurring in humans/animals. Any inhomogeneity or deviation from the natural sequence is, however, unacceptable in many cases because these products frequently show different immunological (for example induction of antibody formation) and pharmacological (half-life, pharmacokinetics) properties. For these reasons, it is necessary in most cases to produce a nature-identical product (homogeneous and without foreign amino acids at the N-terminus).

On natural expression, for example in humans, many pharmaceutical proteins which are in use are transported into the extracellular space, and cleavage of the signal sequence present in the precursor protein for this purpose results in a clearly defined N-terminus. Such a homogeneous N-terminus is not always easy to produce, for example in bacterial cells, for several reasons.

The synthesis of all cytoplasmic proteins in prokaryotic microorganisms starts with a methionine due to the start codon ATG, which is both a translation initiation site and the codon for methionine. Depending on the structure of the second amino acid after the N-terminal methionine, this methionine may be cleaved off by a host cell methionine-aminopeptidase (MAP) leading to a mixture of a product starting either with Met or with the second amino acid. The separation of these two species is very difficult and leads to reduced yields. In recombinant cytoplasmic production of a polypeptide it is usual for a not inconsiderable proportion (1-50%) of the polypeptide to remain unaffected by the MAP. Therefore, production of recombinant polypeptides using a cytoplasmic Met-expression system is often highly unfavorable.

Another possibility to produce a mature recombinant polypeptide via a cytoplasmic pathway is the production of an N-terminal fusion protein with subsequent chemical or enzymatic in vitro cleavage. However, in many cases N-terminus of the fusion protein is not easily accessible to enzymatic cleavage leading to low cleavage rates or no cleavage at all. This may be due to the N-terminus being structurally inaccessible.

In addition, recombinant proteins are expressed in the cytoplasm of prokaryotic microorganisms in a reduced state with the effect that disulphide bonds often necessary for correct protein folding and function are not formed or not formed correctly. Recombinant polypeptides containing disulphide bonds therefore may necessitate difficile in vitro oxidation.

Also, cytoplasmic expression leads often to the formation of inclusion bodies, which have to be solubilised under denaturing conditions followed by a refold to the native structure prior to the actual purification process.

Periplasmic expression, on the other hand, could directly yield a product with the desired properties:
(i) Correct, mature N-terminus by cleaving off of a periplasmic signal sequence by the host cell's signal peptidase apparatus
(ii) Soluble expression due to correct folding
(iii) Correct disulphide bond formation due to oxidative milieu in the periplasm very similar to the one found in the human extracellular fluid (where this molecule is naturally found)

Accordingly, it is therefore an object of the present invention to provide a periplasmic expression system which is suitable for the production of a recombinant polypeptide of interest in a prokaryotic host cell.

It has now surprisingly been found within the context of the present invention that an expression vector encoding the signal sequence of the glutaryl 7-ACA acylase gene (gac gene) of *Pseudomonas diminuta* and a polypeptide of interest is particularly suitable for use in a process for the recombinant production of the polypeptide.

In one aspect, the present invention thus relates to an expression vector comprising a polynucleotide encoding a fusion protein comprising the signal sequence of the gac gene of *Pseudomonas diminuta* and a polypeptide of interest other than gac of *Pseudomonas diminuta*, wherein said signal sequence and said polypeptide of interest are linked in such a way that upon expression of the polynucleotide in a suitable host cell the signal sequence is cleaved off the fusion protein and the polypeptide of interest is released into the periplasm of the host cell.

In accordance with the present invention, a variety of polypeptides of interest can be produced by utilization of the expression vector. For example, the polypeptide of interest can be selected from the group consisting of an interferon, an interleukin, a growth hormone, a growth factor, a cytokine, an enzyme, an enzyme inhibitor, an antibody and an antibody fragment, and the like, for example interferon alpha 2A, interferon alpha 2B, interleukin-3, interleukin-6, human growth hormone, insulin, granulocyte-colony stimulating factor, granulocyte macrophage-colony stimulating factor, macrophage-colony stimulating factor, interferon beta 1, bovine somatropin, porcine somatropin, interleukin-11, interleukin-2, a Fab-fragment, and small peptides such as calcitonin, parathyroid hormone (PTH), or a glucagon. Preferably, within the scope of the present invention, the polypeptide of interest is a recombinant human interferon 2, in particular human interferon alpha 2A or human interferon alpha 2B, the latter being particularly preferred to be the polypeptide of interest.

With respect to the polynucleotide encoding the part of the fusion protein which is the polypeptide of interest, a cDNA or a synthetic polynucleotide can be used. If a given cDNA or synthetic polynucleotide corresponding to a natural occurring gene sequence will be expressed only poorly, the structure of the cDNA or synthetic polynucleotide may be adapted to the respective host cell by codon optimization.

In this respect, within a preferred embodiment of the present invention, the polynucleotide encoding the polypeptide of interest being rhIFNα2B, will comprise the following nucleotide sequence (SEQ ID NO 1)

5'-TGC GAT CTG CCG CAA ACC CAC AGC CTG GGT AGC CGG

CGA ACC TTG ATG CTT CTG GCA CAG ATG CGG CGA ATC

TCT CTT TTC TCT TGC TTA AAG GAT CGA CAT GAC TTC

GGT TTC CCG CAG GAG GAG TTC GGT AAC CAG TTC CAA

AAG GCT GAA ACC ATC CCG GTA TTG CAT GAG ATG ATC

CAG CAG ATC TTC AAC CTG TTC AGC ACT AAG GAC TCT

TCT GCT GCT TGG GAT GAG ACC CTG CTT GAC AAA TTC

TAC ACT GAA CTG TAC CAG CAG CTG AAC GAC CTG GAA

GCC TGC GTG ATC CAG GGT GTG GGT GTG ACT GAG ACT

CCG CTG ATG AAG GAG GAC TCT ATT CTG GCT GTG CGA

AAA TAC TTC CAA CGG ATC ACT CTG TAT CTG AAA GAG

AAG AAA TAC AGC CCG TGC GCC TGG GAG GTT GTC CGA

GCA GAA ATC ATG CGG TCT TTC TCT TTG TCT ACC AAC

TTG CAA GAA TCT TTA CGA AGC AAG GAA-3', where 48 out of 165 codons of the natural occurring human interferon alpha 2B have been altered with respect to the nucleotide sequence without changing the amino acid sequence.

With respect to the *Pseudomonas diminuta* strain, any *Pseudomonas diminuta* strain which exhibits a glutaryl-7-aminocephalosporic acid acylase activity will bear a gac gene encoding a suitable signal sequence.

For example, such a *Pseudomonas diminuta* strain has been described in Czech Patent No. CZ 278,515 under designation no. CCM 3987.

Such a *Pseudomonas diminuta* strain bears the gene encoding the enzyme glutaryl-7-ACA-acylase, abbreviated gac.

A preferred embodiment of the present invention relates to the expression vector according to the present invention, wherein said signal sequence of the gac gene of *Pseudomonas diminuta*, forming part of the said fusion protein, comprises the amino acid sequence (SEQ ID NO 2)

MLRVLHRAASALVMATVIGLAPAVAFA.

For example, such amino acid sequence may be encoded by the following polynucleotide sequence (SEQ ID NO 3)

5'-ATG CTG AGA GTT CTG CAC CGG GCG GCG TCC GCC TTG

GTT ATG GCG ACT GTG ATC GGC CTT GCG CCC GCC GTC

GCC TTT GCG-3'

Likewise, polynucleotide sequence where nucleotides have been altered as to create restriction enzyme site can be used as long as such mutations are silent, i.e. they do not change the amino acid sequence of the gas signal sequence as outlined above.

Accordingly, another example for a suitable polynucleotide sequence encoding the gac signal sequence may be (SEQ ID NO 4)

5'-ATG CTG AGA GTT CTG CAC CGG GCG GCG TCC GCC TTG

GTT ATG GCG ACT GTG ATC GGC CTT GCG CCC GCG GTC

GCC TTT GCG-3', wherein, compared to the polynucleotide sequence mentioned above, a single mutation (C->G) has been introduced with respect to the last nucleotide of codon 23, in order to obtain a restriction enzyme site (Sac II site) which may be used in further cloning.

Another preferred embodiment of the present invention relates to the expression vector according to the present invention, wherein said vector is a plasmid. A low (about 1-10 copies per cell), medium (about 10-50 copies per cell) or high (about >50 copies per cell) copy plasmid may be used. These definitions apply if such a plasmid will be used in a favourable environment, and such copy numbers may be lower under certain fermentation conditions, e.g. under reduced temperature conditions. For strong inducible systems a medium copy basic replicon (e.g. pBR322) may be adaquate, for strong basal expression from low or medium strength expression elements (promoter, RBS, structural gene) a high copy replicon (e.g. plasmids from the pUC series) may be better suited. In the context of the present invention, in particular with respect to production of rhIFNα2B, a high-copy plasmid is preferably used. Accordingly, a further preferred embodiment of the present invention relates to an expression vector according to the present invention, wherein said vector is a high copy plasmid.

Further elements of the expression vector according to the present invention comprise transcription and translation elements, in particular a promoter and a ribosomal binding site (RBS).

For periplasmic expression, the ribosomal binding site should neither be too strong nor too weak. The first could lead to an overstrain of the periplasmic protein export apparatus (translocase etc.) and the deposition of (often insoluble) uncleaved fusion protein in the cytoplasm. The second could lead to poor protein yields. The situation on the transcriptional level (promoter) is similar to the one on the translational level (RBS). Transcription should neither be too strong nor to weak in order to avoid the described phenomena. Also, the sudden onset of protein production when using an inducible promoter may cause problems with "clogging" the export apparatus or will at least require extensive fine-tuning of the induction step and fermentation parameters. This will often lead to non-robust processes.

It has been found that in the context of the present invention the promoter region and the ribosomal binding site of the gac gene of *Pseudomonas diminuta* are particularly suitable for serving as transcriptional and translational regulatory elements.

Therefore, a preferred embodiment comprises an expression vector according to the present invention, wherein said vector further comprises a polynucleotide comprising the promoter region and the ribosomal binding site of the gac gene of *Pseudomonas diminuta*, which polynucleotide being operatively linked to the polynucleotide encoding the fusion protein comprising the signal sequence and the polypeptide of interest.

In a further preferred embodiment thereof said polynucleotide comprising the promoter region and the ribosomal binding site comprises the nucleotide sequence (SEQ ID NO 5)

5'-ATCCTGGTTCGTACGCGCCGCCTACAAGTGGTGATCTAGGGGAACGT

TCCGGGGGCGTCGCTGCAACGGCGTCTCCGGATCTGGGTGAGAGGGGAAA

TCC-3'

In a yet further preferred embodiment thereof said polynucleotide comprising the promoter region and the ribosomal binding site comprises the nucleotide sequence (SEQ ID NO 6)

5'-TCTAGACCAACAACATCTTCAACGTCTACCCGACCAAGATTCAGGAG

CCGTCGGCCGACCTGGGCAATGGGATGTACAGCGGGCTTGCGCCGTTCGG

CTTCACCGGCGGATCCTGGTTCGTACGCGCCGCCTACAAGTGGTGATCTA

GGGGAACGTTCCGGGGGCGTCGCTGCAACGGCGTCTCCGGATCTGGGTGA

GAGGGGAAATCC-3'.

Further elements may be present in an expression vector according to the present invention, as appropriate.

For example, an expression vector according to the present invention may comprise a polynucleotide comprising one or more transcription terminator(s).

Likewise, an expression vector according to the present invention may comprise a polynucleotide encoding one or more selectable markers, e.g. to provide for antibiotic resistance of a transformed host cell. Suitable selectable markers are widely known in the art. In the context of the present invention, the expression vector favourably comprises a polynucleotide comprising a tetracycline resistance gene.

Additionally, where suitable, further regulatory elements may be present on an expression vector according to the present invention. Regulatory elements are widely known in the art, like a repressor or an enhancer.

In a further aspect, the present invention relates to prokaryotic host cells which are transformed with an expression vector according to the present invention in order to be capable of bring about expression of the polypeptide of interest.

Therefore, the present invention relates to a prokaryotic host cell transformed with an expression vector which is compatible with the host cell, said vector comprising a polynucleotide encoding a fusion protein comprising the signal sequence of the gac gene of *Pseudomonas diminuta* and a polypeptide of interest other than gac of *Pseudomonas diminuta*, wherein said signal sequence and said polypeptide of interest are linked in such a way that upon expression of the polynucleotide in a suitable host cell the signal sequence is cleaved off the fusion protein and the polypeptide of interest is released into the periplasm of the host cell.

Examples for suitable polypeptides of interest are those as mentioned above. A preferred embodiment thereof relates to such a prokaryotic host cell, wherein the polypeptide of interest is an interferon alpha 2. In particular, such interferon alpha 2 is selected from the group consisting of interferon alpha 2A and interferon alpha 2B, the latter being preferred.

Another preferred embodiment thereof relates to a host cell according to the present invention, wherein said vector is a plasmid, preferably a high copy plasmid.

The present invention further relates to a host cell according to the present invention, wherein said signal sequence of the gac gene of *Pseudomonas diminuta* comprises the amino acid sequence (SEQ ID NO 2)

MLRVLHRAASALVMATVIGLAPAVAFA.

In a further aspect, the present invention relates to the host cell according to the present invention, wherein vector further comprises a polynucleotide comprising the promoter region and the ribosomal binding site of the gac gene of *Pseudomonas diminuta*, which polynucleotide being operatively linked to the polynucleotide encoding the fusion protein comprising the signal sequence and the polypeptide of interest.

Such polynucleotide comprising the promoter region and the ribosomal binding site preferably comprises the nucleotide sequence (SEQ ID NO 5)

5'-ATCCTGGTTCGTACGCGCCGCCTACAAGTGGTGATCTAGGGGAACGT

TCCGGGGGCGTCGCTGCAACGGCGTCTCCGGATCTGGGTGAGAGGGGAAA

TCC-3'.

In a further preferred embodiment thereof, such polynucleotide comprising the promoter region and the ribosomal binding site comprises the nucleotide sequence (SEQ ID NO 6)

5'-TCTAGACCAACAACATCTTCAACGTCTACCCGACCAAGATTCAGGAG

CCGTCGGCCGACCTGGGCAATGGGATGTACAGCGGGCTTGCGCCGTTCGG

CTTCACCGGCGGATCCTGGTTCGTACGCGCCGCCTACAAGTGGTGATCTA

GGGGAACGTTCCGGGGGCGTCGCTGCAACGGCGTCTCCGGATCTGGGTGA

GAGGGGAAATCC-3'.

With respect to prokaryotic host cells, preferably said host cell according to the present invention is a GRAM-negative bacterial cell. Preferably such a bacterial cell is selected from the group consisting of *Escherichia coli* (*E. coli*), *Pseudomonas* sp., *Enterobacter* sp., *Campylobacter* sp., and *Vitreoscilla* sp, *E. coli* being particularly preferred. Preferably, derivatives of *E. coli* K 12 will be used because such strains have a long history of safe use and are particularly suitable for periplasmatic expression. Likewise, other types of *E. coli*, e.g. *E. coli* B derivatives, may be used.

In a preferred embodiment of the present invention, the prokaryotic host cell is derived from *E. coli* W3110 (ATCC 27325). Such a strain has been deposited with the American Type Culture Collection (ATCC), 10801 University Boulevard, Manassas, Va. 20110-2209, USA on Feb. 28, 2001, under the Designation No. PTA-3132.

*E. coli* W3110 (ATCC 27325) and the deposited strain ATCC PTA-3132 can genetically be characterized as follows:

*Escherichia coli* K-12 [F⁻ mcrA mcrB IN(rrnD-rrnE)I lambda⁻].

A further aspect of the present invention relates to a process for production of a polypeptide of interest, comprising (i) providing a prokaryotic host cell transformed with an expression vector which is compatible with the host cell, said vector comprising a polynucleotide encoding a fusion protein comprising the signal sequence of the gac gene of *Pseudomonas diminuta* and a polypeptide of interest other than gac of *Pseudomonas diminuta*, wherein said signal sequence and said polypeptide of interest are linked in such a way that upon expression of the polynucleotide in a suitable host cell the signal sequence is cleaved off the fusion protein and the polypeptide of interest is released into the periplasm of the host cell, and (ii) culturing the prokaryotic host cell under conditions which cause expression of the polynucleotide whereby upon formation of the fusion protein the signal sequence is cleaved off the fusion protein and the polypeptide of interest is released into the periplasm of the host cell.

Optionally, the process according to the present invention further comprises isolation of the polypeptide of interest.

Examples for suitable polypeptides of interest are those as mentioned above. A preferred embodiment thereof relates to such a prokaryotic host cell, wherein the polypeptide of interest is an interferon alpha 2. In particular, such interferon alpha 2 is selected from the group consisting of interferon alpha 2A and interferon alpha 2B, the latter being preferred.

Another preferred embodiment thereof relates to the process according to the present invention, wherein said vector is a plasmid, preferably a high copy plasmid.

The present invention further relates to a process according to the present invention, wherein said signal sequence of the gac gene of *Pseudomonas diminuta* comprises the amino acid sequence (SEQ ID NO 2)

MLRVLHRAASALVMATVIGLAPAVAFA.

In a further aspect, the present invention relates to the process according to the present invention, wherein said vector further comprises a polynucleotide comprising the promoter region and the ribosomal binding site of the gac gene of *Pseudomonas diminuta*, which polynucleotide being operatively linked to the polynucleotide encoding the fusion protein comprising the signal sequence and the polypeptide of interest.

Such polynucleotide comprising the promoter region and the ribosomal binding site preferably comprises the nucleotide sequence (SEQ ID NO 5)

5'-ATCCTGGTTCGTACGCGCCGCCTACAAGTGGTGATCTAGGGGAACGT

TCCGGGGGCGTCGCTGCAACGGCGTCTCCGGATCTGGGTGAGAGGGGAAA

TCC-3'.

In a further preferred embodiment thereof, such polynucleotide comprising the promoter region and the ribosomal binding site comprises the nucleotide sequence (SEQ ID NO 6)

5'-TCTAGACCAACAACATCTTCAACGTCTACCCGACCAAGATTCAGGAG

CCGTCGGCCGACCTGGGCAATGGGATGTACAGCGGGCTTGCGCCGTTCGG

CTTCACCGGCGGATCCTGGTTCGTACGCGCCGCCTACAAGTGGTGATCTA

GGGGAACGTTCCGGGGGCGTCGCTGCAACGGCGTCTCCGGATCTGGGTGA

GAGGGGAAATCC-3'.

With respect to prokaryotic host cells, preferably said host cell according to the present invention is an *E. coli* cell; implications of that have been described in detail above.

In a further embodiment the present invention relates to the cultivation (or fermentation) part of the process utilizing the transformed host cell according to the present invention.

Many factors can influence the productivity of fermentation processes employing recombinant organisms. The applied fermentation strategy has to consider the sensitive relationships between microbial physiology and plasmid copy number, plasmid stability and gene expression which is not only determined on gene's level but also by media composition and process conditions. Besides the stability of the host strain, stability of the product is of great importance for high level production of recombinant proteins.

For the development of a fermentation process employing a constitutive expression system, growth conditions and recombinant product formation are closely related to each other. Therefore the effort for optimal growth and control of growth conditions which are in a close relationship to product formation during the whole fermentation run is higher compared to induced expression systems.

Typical *E. coli* fermentation processes for the production of recombinant proteins are characterized by short fermentation times in a range between a few hours and about 100 hours of cultivation. Most often not only a carbon source but also various complex or inorganic nitrogen sources, different salts and trace elements are fed to *E. coli* cultures. Carbon feeding usually follows time-profiles with a stepwise increase or exponential increase of the feeding rates. Sometimes also mixtures of carbon sources are used during *E. coli* fermentations. Feeding of the carbon source is usually coupled to the oxygen transfer capacity of the bioreactor by the use of various control strategies.

A further object of the present invention is to provide a robust and reproducible fermentation process, based on the gac expression system and corresponding transformed host cells according to the present invention, for high yield periplasmatic expression of a polypeptide of interest without the use of extensive nitrogen source feeding and optionally without the addition of trace elements to the fermentation media.

The process according to the invention is carried out in principle by initially cultivating the bacterial host cell, i.e. the expression strain, in accordance with microbiological practice known per se. The strain is generally brought up starting from a single colony on a nutrient medium, but it is also possible to employ cryopreserved cell suspensions (cell banks). The strain is generally cultivated in a multistage process in order to obtain sufficient biomass for further use.

On a small scale, this can take place in shaken flasks, wherein it is possible in most cases to employ a complex medium (for example LB broth). However, it is also possible to use defined media (for example citrate medium). For the cultivation, a small-volume preculture of the host strain (inoculated with a single colony or with a cell suspension from a cryoculture) is grown, the temperature for this cultivation not generally being critical for the later expression result, so that it is possible routinely to operate at relatively high temperatures (for example 30° C. or 37° C.). The main culture is set up in a larger volume (for example 500 ml), where it is in particular necessary to ensure good aeration (large volume of flask compared with the volume of contents, high speed of rotation). Since it is intended that expression takes place in soluble form, the main culture will in most cases also be carried out at a somewhat lower temperature (for example 22° C. or 28° C.). Both inducible systems (for example with trp, lac, tac or phoA promoter) and constitutive systems (like the preferred system of the present invention comprising the gac promoter) are suitable for producing soluble proteins. The resulting cells can be harvested and processed further.

On a larger scale, the multistage system consists of a plurality of bioreactors (fermenters), preferably employing defined nutrient media in order to be able to improve the process engineering control of the process or employing complex nutrient media in order to enhance growth of the microorganism and to increase robustness of the process. In addition, it is possible to greatly increase biomass and product formation by feeding of particular nutrients (fed batch mode). For example, a preliminary stage fermenter and a main stage fermenter are used. The preliminary stage fermenter is inoculated with a so-called Inoculum which is generally grown from a single colony or a cryoculture in a shake flask. Good aeration must also be ensured in the fermenter—and especially in the main stage thereof. The resulting cells are once again delivered for further processing.

Accordingly, in a preferred embodiment the culturing (or cultivation) of the process according to the present invention as described herein is being performed as a multi-stage process comprising a pre-culture step and a main culture step. In the alternative, a single-step fermentation without a pre-culture step is possible. In an even more preferred embodiment, the process according to the present invention as described herein is being performed as a multi-stage fermentation process comprising a shake-flask step, optionally a pre-culture step, and a main-culture step.

In particular, said culturing of the procaryotic host cell in the main culture step is performed in a culture medium comprising a substrate for more than about 90% of the cultivation time at a substrate concentration lower than the saturation constant of the substrate, accompanied by high levels of dissolved oxygen concentration, and further accompanied by a steadily decreasing specific growth rate of the bacterial host cells, the process being performed at a temperature which is lower than the optimum temperature for growth of the host cell.

In this context, the saturation constant is the concentration of a substrate (in particular the carbon source) at which the host cell is growing at a specific growth rate which is equivalent to 50% of the maximum specific growth rate.

In this context, the specific growth rate is the increase of biomass concentration in a certain time interval divided by the average biomass concentration of said time interval.

Preferably, the culture medium of the main culture as well as, where applicable, of the pre-culture, is a complex medium comprising a complex nitrogen source, preferably a yeast extract, various salts and a carbon source to support initial growth of the host cell. In a preferred embodiment thereof, said carbon source is either added to the main culture medium by feeding of said carbon source after inoculation or, preferably, present in the main culture at the time of inoculation.

Preferably, the concentration of dissolved oxygen in the main culture step is higher than about 20%, more preferably from about 40% up to about 100% of saturation.

Preferably, the steadily decreasing growth rate in the main culture step is from about 2 h$^{-1}$ to about 0.001 h$^{-1}$.

In a preferred embodiment, the temperature in the main culture step is between about 22° C. and about 35° C., preferably between about 25° C. and about 31° C., most preferably about 28° C.

In another preferred embodiment, said cultivation in the pre-culture and/or main culture is performed at a pH value in the range of about 6.7 to about 7.3.

In a further preferred embodiment of the present invention, the substrate is glycerol or, preferably, a carbohydrate. Preferably, the carbohydrate is glucose.

As mentioned herein, examples for suitable proteins of interest are those as mentioned above. A preferred embodiment, the polypeptide of interest is an interferon alpha 2. In particular, such interferon alpha 2 is selected from the group consisting of interferon alpha 2A and interferon alpha 2B, the latter being preferred.

In a most preferred embodiment regarding all aspects of the processes of the present invention, the host cell is an *E. coli* cell.

The polypeptide of interest can then be isolated by protein purification methods known to the skilled person (see, for example, M. P. Deutscher, in: Methods in Enzymology: Guide to Protein Purification, Academic Press Inc., (1990), 309-392). A purification sequence generally comprises a cell disruption step, a clarification step (centrifugation or microfiltration) and various chromatographic steps, filtrations and/or precipitations. A suitable example for the isolation of a polypeptide of interest produced in accordance with the present invention is given below.

Deposition of Microorganisms:

*E. coli* strain W3110 (ATCC 27325) has been deposited with the American Type Culture Collection (ATCC), 10801 University Boulevard, Manassas, Va. 20110-2209, USA on Feb. 28, 2001, under the Designation No. PTA-3132.

The following examples serve to illustrate the present invention, without in any way limiting the scope thereof. Subject-matter disclosed in the examples relates to preferred embodiments of the present invention.

EXAMPLES

Example 1

Construction of a Host Cell Strain for Production of Recombinant Human Interferon Alpha 2B (rhIFNα2B)

1.1 General Considerations

The polypeptide rhIFNα2b (recombinant human Interferon-α2b) is produced in the *Escherichia coli* K-12 strain W3110 transformed with a plasmid containing an optimized synthetic gene coding for rhIFNα2b. rhIFNα2b is produced under the control of the promoter and Ribosome Binding Site (RBS) of the glutaryl 7-ACA acylase gene (gac) from *Pseudomonas diminuta* CCM 3987 by fermentation of recombinant *E coli* K-12. rhIFNα2b is expressed as an N-terminal fusion protein with the signal sequence from the same (gac) gene, directing the protein to the periplasm with concurrent processing (cleaving off) of the signal sequence. The fermentation process therefore directly yields mature rhIFNα2b with a primary sequence identical to that of naturally occurring human Interferon alpha 2b. The expression plasmid is designated pMG414, the production strain W3110 [pMG414].

1.2 Construction of Expression Vector pMG414 pUC19 serves as the starting point for the construction of the vector plasmid. pUC19 is a frequently used and thoroughly characterized high copy plasmid. It contains a highly efficient origin of replication and an ampicillin resistance (amp or bla) gene (Yanisch-Perron et al., 1985; Vieira and Messing, 1982; GenBank accession numbers L09137 and X02514).

Even though pUC19 is frequently used for the construction of expression plasmids, the amp gene may not be an ideal selectable marker for industrial purposes. For this reason the promoter and the coding region of the amp gene are removed and replaced by the promoter and the coding region of the tetracycline resistance gene (tet) from the well known safety plasmid pBR322 (Bolivar et al., 1977a, 1977b, 1978; review: Balbás et al., 1986; GenBank accession numbers J01749, K00005, L08654, M10283, M10286, M10356, M10784, M10785, M10786, M33694, V01119). This cloning work is performed with the help of high fidelity PCR techniques.

To achieve this, the fragment spanning bps 1743 to 679 of pUC19 is amplified using high fidelity PCR (Pwo DNA Polymerase system from Roche Biochemicals) and the following 5'-phosphorylated oligonucleotides:

```
Oligo 235:
                                       (SEQ ID NO 7)
5'- Phosphate - TAACTGTCAG ACCAAGTTTA CTC -3'

Oligo 236:
                                       (SEQ ID NO 8)
5'- Phosphate - GCGTTTCGGT GATGACGGTG -3'
```

The resulting PCR fragment is 1624 bps in length and contains the complete pUC19 backbone lacking the amp promoter and coding sequence, but including the stop codon and transcription terminator from the amp gene.

As mentioned above, the tet promoter and coding sequence (excluding the stop codon) is amplified from pBR322. Again, high fidelity PCR was used to amplify bps 4 to 1273 of pBR322. The following 5'-phosphorylated oligonucleotides were used for this amplification:

```
Oligo 237:
                                       (SEQ ID NO 9)
5'- Phosphate - TCATGTTTGA CAGCTTATCA TCG -3'

Oligo 238:
                                       (SEQ ID NO 10)
5'- Phosphate - GGTCGAGGTG GCCCGGCTC -3'
```

The resulting PCR fragment is 1270 bps in length. The two PCR fragments are purified by preparative agarose gel electrophoresis and ligated using T4 DNA Ligase (Rapid DNA Ligation Kit, Roche Biochemicals). The ligated DNA is purified and electroporated into *Escherichia coli* K-12 DH10B (Life Technologies ElectroMAX DH10B electrocompetent cells, genotype: F⁻ mcrA Δ(mrr-hsdRMS-mcrBS) φ80dlacZΔM15 ΔlacX74 deoR recA1 endA1 araD139 Δ(ara, leu)7697 galU galk λ⁻ rpsL nupG). Transformed cells are plated on to LB agar 15 mg/L tetracycline and 3 g/L glucose. Liquid cultures are grown in LB broth containing 15 mg/L tetracycline and 3 g/L glucose and plasmid DNA is isolated from these cultures using standard miniprep methods. Plasmid DNAs are analyzed by restriction analysis for correct integration of the tet fragment into the pUC19 backbone. Since integration of the fragment was unspecific with respect to orientation, only about 50% of all insert containing clone had the fragment inserted in the correct orientation, i.e. the tet gene running in the same direction as the the amp gene in pUC19. A larger amount of DNA is isolated from liquid cultures of a few clones and subjected to more detailed restriction analyses. Of those clones showing correct restriciton patterns, one is selected for further cloning work.

The respective plasmid was designated pMG402. It is identical to pUC19 in all features and functions but for the fact that it must be grown on/in tetracycline-containing media instead of ampicillin-containing media. This way a tet resistant high copy vector suitable for industrial purposes is generated.

Features of plasmid pMG402:

bps 1954-680: pUC19 backbone (=pUC19 lacking the amp promoter and structural gene)

bps 681-1953: tet promoter and structural gene from pBR322 rhIFNα2b is expressed as an N-terminal fusion with the signal sequence of glutaryl 7-ACA acylase from *Pseudomonas diminuta* CCM 3987 (gac1ss=SEQ ID NO 2) directing the protein to the periplasm with concurrent processing (cleaving off) of the signal sequence by the host cell's signal peptidase apparatus.

Amino acid sequence of gac1ss (27 aa): MLRVLHRAAS ALVMATVIGL APAVAFA

In the 3' region of the coding sequence of the gac1ss a Sac II restriction endonuclease site is introduced via the 3' PCR primer creating a silent mutation (amino acid sequence unchanged). This Sac II site allows fusion of the gac1ss coding region with the rhIFNα2b gene.

The structural gene for rhIFNα2b is synthesized chemically. It differs from the natural human cDNA sequence in 48 of 165 codons and is designed to eliminate any weak and error prone codons.

In the following table, codon changes are indicated. In the table, "Natural codon" refers to the cDNA sequence published by Streuli et al., 1980 (GenBank Accession Number V00548). The amino acid numbers refer to mature hIFNα2b (starting with Cys 1). The amino acid sequence to be encoded by the synthetic gene is taken from the SwissProt Database, Assession number P01563/P01564 (amino acids 24 to 188).

| Exchange no. | Amino acid | Natural codon | Synthetic codon |
|---|---|---|---|
| 1 | Cys 1 | TGT | TGC |
| 2 | Pro 4 | CCT | CCG |
| 3 | Arg 12 | AGG | CGG |
| 4 | Arg 13 | AGG | CGA |
| 5 | Leu 17 | CTC | CTT |
| 6 | Arg 22 | AGG | CGG |
| 7 | Arg 23 | AGA | CGA |
| 8 | Ser 28 | TCC | TCT |
| 9 | Leu 30 | TTG | TTA |
| 10 | Asp 32 | GAC | GAT |
| 11 | Arg 33 | AGA | CGA |
| 12 | Phe 36 | TTT | TTC |
| 13 | Gly 37 | GGA | GGT |
| 14 | Phe 38 | TTT | TTC |
| 15 | Pro 39 | CCC | CCG |
| 16 | Phe 43 | TTT | TTC |
| 17 | Gly 44 | GGC | GGT |
| 18 | Pro 54 | CCT | CCG |
| 19 | Val 55 | GTC | GTA |
| 20 | Leu 56 | CTC | TTG |
| 21 | Asn 65 | AAT | AAC |
| 22 | Leu 66 | CTC | CTG |
| 23 | Thr 69 | ACA | ACT |
| 24 | Ser 72 | TCA | TCT |
| 25 | Leu 80 | CTC | CTG |
| 26 | Leu 81 | CTA | CTT |

-continued

| Exchange no. | Amino acid | Natural codon | Synthetic codon |
|---|---|---|---|
| 27 | Leu 88 | CTC | CTG |
| 28 | Asn 93 | AAT | AAC |
| 29 | Cys 98 | TGT | TGC |
| 30 | Ile 100 | ATA | ATC |
| 31 | Gly 102 | GGG | GGT |
| 32 | Gly 104 | GGG | GGT |
| 33 | Thr 106 | ACA | ACT |
| 34 | Pro 109 | CCC | CCG |
| 35 | Ser 115 | TCC | TCT |
| 36 | Arg 120 | AGG | CGA |
| 37 | Arg 125 | AGA | CGG |
| 38 | Leu 128 | CTC | CTG |
| 39 | Pro 137 | CCT | CCG |
| 40 | Cys 138 | TGT | TGC |
| 41 | Arg 144 | AGA | CGA |
| 42 | Arg 149 | AGA | CGG |
| 43 | Phe 151 | TTT | TTC |
| 44 | Ser 154 | TCA | TCT |
| 45 | Thr 155 | ACA | ACC |
| 46 | Ser 160 | AGT | TCT |
| 47 | Arg 162 | AGA | CGA |
| 48 | Ser 163 | AGT | AGC |

The resulting gene allows efficient and precise transcription and translation of rhIFNα2b in *Escherichia coli*. Since the gene is designed for expression in a bacterial system it does not contain any untranslated sequences (introns etc.).

The structural gene is chemically synthesized. In brief, overlapping complementary oligonucleotides about 30 to 50 nucleotides in length are synthesized in a way to cover both strands of the structural gene sequence without any gaps. The oligonucleotides are hybridized to each other and ligated using T4 DNA Ligase. The reaction product is cut with restriction endonucleases and cloned into the pUC18 vector. The resulting plasmid is sequenced and shows the correct sequence.

The synthetic gene on this plasmid does not contain the gac signal sequence. This part of the coding region is introduced via the gac fragment containing promoter, RBS and signal sequence and fused to the rhIFNα2b structural gene.

The gac fragment is generated by chemical synthesis. For example, overlapping complementary oligonucleotides about 30 to 50 nucleotides in length are synthesized in a way to cover the full length of both strands of the gac fragment (including the restriction endonuclease recognition sites on both sides plus a minimum of 6 additional basepairs to allow efficient cleavage) without any gaps. The oligonucleotides are then hybridized to each other (e.g. by heating and subsequent cooling) and ligated using T4 DNA Ligase. The reaction product is then cut with the respective restriction endonucleases (Xba I and EcoR I) and cloned into the pMG402 vector (see below).

In the alternative, the gac fragment containing promoter, RBS and signal sequence can be amplified from a plasmid comprising such elements like plasmid pKS55, which construction is described in CS patent No. 278,515. The gac gene cloned therein has been derived from a strain of *Pseudomonas diminuta* (CCM 3987). Amplification is carried out using a high fidelity PCR system. The restriction endonuclease sites needed for cloning are introduced via the following PCR primers.

Primers:

```
                                          (SEQ ID NO 11)
1. 5'-Phosphate - GGGGGGTCTAGACCAACAACATCTTCAACGTC
TACC -3'

(SEQ ID NO 12)
2. 5'-Phosphate - CC CCC CGA ATT CAC TAG TAC GCG
TCT CTC TCC -3'
```

There will be no difference in performance between a gac fragment generated via high fidelity PCR amplification and a gac fragment generated by chemical synthesis.

The thus created gac fragment has the following nucleotide sequence (SEQ ID NO 13):

```
5'-GGGGGGTCTAGACCAACAACATCTTCAACGTCTACCCGACCAAGATT

CAGGAGCCGTCGGCCGACCTGGGCAATGGGATGTACAGCGGGCTTGCGCC

GTTCGGCTTCACCGGCGGATCCTGGTTCGTACGCGCCGCCTACAAGTGGT

GATCTAGGGGAACGTTCCGGGGGCGTCGCTGCAACGGCGTCTCCGGATCT

GGGTGAGAGGGGAAATCCATGCTGAGAGTTCTGCACCGGGCGGCGTCCGC

CTTGGTTATGGCGACTGTGATCGGCCTTGCGCCCGCGGAGAGAGACGCGT

ACTAGTGAATTCGGGGGG-3'
```

The gac fragment (either synthetic or created via PCR) and the vector plasmid pMG402 are ligated using the Xba I and EcoR I sites. This way the expression vector pMG412 is generated.

The expression vector, pMG412, contains codons 1-23+ the first nucleotide of codon 24 of the gac signal sequence. Into codons 22-24 the Sac II site is introduced by silent mutation. Anything downstream of the Sac II site in pMG412 is primer or vector sequence.

The last two nt of codon 24+codons 25-27 are introduced by the forward PCR primer for the target structural gene (rhIFNα2B, see above). Such a primer therefore contains the following elements:

Cutting overhang (e.g. 6 nucleotides)—Sac II site—to gcc ttt gcg (SEQ ID NO 14)—hybridizing region corresponding to the 5' end of the "mature" target gene.

In particular, a suitable primer has the following nucleotide sequence (SEQ ID NO 15):

```
TT GCG CCC GCG GTC GCC TTT GCG -
``` hybridizing region (Sac II underlined)

The last amino acids (24-27) of the gac signal sequence are V A F A (SEQ ID NO 16).

From the plasmid construct described above the rhIFNα2b gene is amplified using a high fidelity PCR system. The 5' PCR primer contains the Sac II site for fusing the gene with the gac fragment plus the last four codons of the gac signal sequence. The 3' primer contains the TAA (ochre) stop codon and the Mlu I site for cloning. The amplification of the Interferon alpha structural gene generates the following fragment (SEQ ID NO 17):

GGGGGG<u>CCGCGG</u>TCGCCTTTGCGTGCGATCTGCCGCAAACCCACAGCCTG

GGTAGCCGGCGAACCTTGATGCTTCTGGCACAGATGCGGCGAATCTCTCT

TTTCTCTTGCTTAAAGGATCGACATGACTTCGGTTTCCCGCAGGAGGAGT

TCGGTAACCAGTTCCAAAAGGCTGAAACCATCCCGGTATTGCATGAGATG

ATCCAGCAGATCTTCAACCTGTTCAGCACTAAGGACTCTTCTGCTGCTTG

GGATGAGACCCTGCTTGACAAATTCTACACTGAACTGTACCAGCAGCTGA

ACGACCTGGAAGCCTGCGTGATCCAGGGTGTGGGTGTGACTGAGACTCCG

CTGATGAAGGAGGACTCTATTCTGGCTGTGCGAAAATACTTCCAACGGAT

CACTCTGTATCTGAAAGAGAAGAAATACAGCCCGTGCGCCTGGGAGGTTG

TCCGAGCAGAAATCATGCGGTCTTTCTCTTTGTCTACCAACTTGCAAGAA

TCTTTACGAAGCAAGGAATAAT<u>ACGCGT</u>GAATTCGGGGGG

This rhIFNα2b PCR fragment and pMG412 are ligated using the Sac II and Mlu I sites. This way the final production/expression plasmid pMG414 was generated. Both strands of pMG414 are sequenced and show no differences to the expected sequence.

Features of plasmid pMG414 (total size 3668 bps):

| bps 2728-256: | pUC19 backbone, part 1 |
| --- | --- |
| bps 257-546: | gac fragment (promoter, RBS, signal sequence) |
| bps 547-1044: | synthetic rhIFNα2b gene (including TAA stop) |
| bps 1045-1454: | cloning sites + pUC19 backbone, part 2 |
| bps 1455-2727: | tet gene from pBR322 (promoter/RBS 1455-1536, coding sequence including TAA stop 1537-2727) |

Thereby, the gac fragment containing promoter, RBS and signal sequence is fused to the rhIFNα2b structural gene—using a restriction endonuclease site at the 3' end of the gac fragment introduced by a PCR primer. The same site is fused to the 5' end of the rhIFNα2b structural gene, also by the way of a PCR primer. So after cloning both elements (gac fragment and rhIFNα2b structural gene) into the basic vector a gene encoding a gac1ss-rhIFNα2b fusion protein is generated. Of its total 192 codons (576 nucleotides) the first 27 encode the gac signal sequence not present in the final protein and amino acids 28 to 192 encode mature rhIFNα2b (165 amino acids, cysteine 1 to glutamic acid 165)

The nucleotide sequence of the expression cassette used in the rhIFNα2b expression plasmid pMG414 (807 bps) (see below) and amino acid sequence of the gac1ss-rhIFNα2b fusion protein is shown as follows (SEQ ID NO 18):

5'-  TCTAGA CCAACAACATCTTCAACGTCTACCCGACCAAGATTCAGGAGCCGTCGGCCGACC
TGGGCAATGGGATGTACAGCGGGCTTGCGCCGTTCGGCTTCACCGGCGGATCCTGGTTCG
TACGCGCCGCCTACAAGTGGTGATCTAGGGGAACGTTCCGGGGGCGTCGCTGCAACGGCG
TCTCCGGATCTGGGTGAGAGGGGAAATCC

ATG CTG AGA GTT CTG CAC CGG GCG GCG TCC GCC TTG GTT ATG GCG
 M   L   R   V   L   H   R   A   A   S   A   L   V   M   A
ACT GTG ATC GGC CTT GCG C CC GCG G TC GCC TTT GCG
 T   V   I   G   L   A   P   A   V   A   F   A

<u>TGC</u> GAT CTG CCG CAA ACC CAC AGC CTG GGT AGC CGG CGA ACC TTG
 C   D   L   P   Q   T   H   S   L   G   S   R   R   T   L
ATG CTT CTG GCA CAG ATG CGG CGA ATC TCT CTT TTC TCT TGC TTA
 M   L   L   A   Q   M   R   R   I   S   L   F   S   C   L
AAG GAT CGA CAT GAC TTC GGT TTC CCG CAG GAG GAG TTC GGT AAC
 K   D   R   H   D   F   G   F   P   Q   E   E   F   G   N
CAG TTC CAA AAG GCT GAA ACC ATC CCG GTA TTG CAT GAG ATG ATC
 Q   F   Q   K   A   E   T   I   P   V   L   H   E   M   I
CAG CAG ATC TTC AAC CTG TTC AGC ACT AAG GAC TCT TCT GCT GCT
 Q   Q   I   F   N   L   F   S   T   K   D   S   S   A   A
TGG GAT GAG ACC CTG CTT GAC AAA TTC TAC ACT GAA CTG TAC CAG
 W   D   E   T   L   L   D   K   F   Y   T   E   L   Y   Q
CAG CTG AAC GAC CTG GAA GCC TGC GTG ATC CAG GGT GTG GGT GTG
 Q   L   N   D   L   E   A   C   V   I   Q   G   V   G   V
ACT GAG ACT CCG CTG ATG AAG GAG GAC TCT ATT CTG GCT GTG CGA
 T   E   T   P   L   M   K   E   D   S   I   L   A   V   R

```
                    -continued
AAA TAC TTC CAA CGG ATC ACT CTG TAT CTG AAA GAG AAG AAA TAC
 K   Y   F   Q   R   I   T   L   Y   L   K   E   K   K   Y
AGC CCG TGC GCC TGG GAG GTT GTC CGA GCA GAA ATC ATG CGG TCT
 S   P   C   A   W   E   V   V   R   A   E   I   M   R   S
TTC TCT TTG TCT ACC AAC TTG CAA GAA TCT TTA CGA AGC AAG GAA
 F   S   L   S   T   N   L   Q   E   S   L   R   S   K   E
TAA

T ACGCGT ACTAGT GAATTC -3'
```

The sequence as shown is divided into sub-paragraphs/regions which comprise:
1. the gac promoter and RBS (first paragraph, bps 257 to 465 of pMG414, see below),
2. the gac signal sequence coding region (second paragraph, bps 466 to 546 of pMG414, see below),
3. the synthetic gene for rhIFNα2b (third paragraph, bps 547 to 1044 of pMG414 (see below)—including the TAA stop codon), and
4. the 3' cloning linker (fourth paragraph, bps 1045 to 1063 of pMG414, see below).

On the pMG414 these four regions are directly joined to one another. They are separated in the figure for reasons of lucidity only.

The start (ATG) and the stop (TAA) codons of the open reading frame are shown in bold.

The first (TGC) an the last (GAA) codon of mature rhIFNα2b are underlined.

The restriction endonuclease sites used for cloning are boxed. These are:
  Xba I (TCTAGA) and EcoR I (GAATTC) for the introduction of the gac fragment (promoter, RBS, signal sequence, Sac II, Mlu I, Spe I sites)
  Sac II (CCGCGG) and Mlu I (ACGCGT) for the introduction of the rhIFNα2b PCR fragment (including four codons for the last four amino acids of the gac1ss, the 495 bp synthetic gene for mature rhIFNα2b, and the TAA(T) stop codon).

The gac promoter shows high constitutive/basal activity, the addition of a chemical inducer or a physical stimulus (change in culture conditions) is not required.

1.3 Cloning and Establishment of the Recombinant Cell Line

The expression plasmid pMG414 is introduced into the host strain ATCC PTA-3132 (=W3110 (ATCC 27325)) by electroporation. Electrocompetent cells are prepared according to a standard protocol, electroporation is carried out in 0.1 mm cuvettes at 1800 V using an Eppendorf Electroporator 2510.

After electroporation the reaction is suspended in liquid medium and plated onto agar plates containing tetracycline.

Starting point for selection of a suitable cell clone is a thus obtained transformation plate. Various clones from this plate are grown in liquid culture and cryopreserved as research cell banks. Their productivity is tested in shake flask experiments and compared. The best clone (E1/116) is used for further development.

The best clone may show good productivity but relatively poor growth. This poor growth can result from various factors, e.g. product toxicity to the host cell, metabolic burden due to product synthesis etc. The addition of glucose often brings some improvement because glucose downregulates (e.g. by catabolite repression) many promoters used for recombinant protein expression. Also, glucose has a general positive effect on the growth of E. coli because it can be directly introduced into the metabolism as a carbon source.

In the case of E1/116, a clear positive effect of glucose on growth is observed. The best results are achieved with glucose concentrations between 2 and 5 g/L. To adapt the cell line to cope with product formation and consequently to better growth in the absence of glucose, the strain is therefore grown in liquid medium in shake flasks for several passages ("shake flask cascade").

More specifically, a cryovial of E1/116 is thawed and the cell suspension streaked onto glucose free LB agar plates containing tetracycline. The plate is incubated at 37° C. until the colonies reach a sufficient size for inoculating a liquid culture. Colonies are transferred from the plate into small shake flasks filled with 15 mL of glucose free LB broth containing tetracycline. The cultures are shaken at 37° C. until they reach an optical density at 600 nm of above 0.5 (typically >1.0). For this first round this takes up to 48 hours due to the poor growth characteristics of the original isolate.

The procedure described in the above paragraph is performed five consecutive times with the liquid culture of the previous round being streaked onto plates and the colonies from the plates serving to inoculate the next liquid culture. From each liquid culture optical density is determined and a sample was taken for determination of product titer using SDS-PAGE—Western Blot. Clones from the culture with the best combination of growth and productivity are the used to initiate the next round.

In the course of the different rounds of this culture cascade (i.e. multiple propagation and reisolation steps) the growth characteristics of the (sub)strain(s) gradually improve. By choosing the strain with the best combination of growth and productivity in each round, titers are also gradually increased. After the fifth round again single colonies are generated on LB agar plates containing tetracycline and used to inoculate a liquid culture containing tetracycline for the generation of a primary seed lot (PSL). The culture is grown at 37° C. to an optical density of about 1.5, mixed with an equal amount of sterile 40% w/v glycerol, aliquoted into cryogenic vials and frozen at −80° C. This PSL is used as a starting point for the generation of the GMP cell banks (Master Cell Bank and Working Cell Bank) of the Interferon alpha 2b production strain. This reisolate is designated E1/116a. Reisolation processes like the one described above have proved to yield reproducible results.

E1/116a shows excellent growth characteristics in shake flasks and stirred bioreactors (fermenters). An inoculum suitable for starting a bioreactor can be grown in a shake flask starting from a Working Cell Bank vial in about 8 hours.

A Master Cell Bank is prepared under cGMP conditions from the primary seed lot described above. In brief, a PSL vial is thawed and plated onto tetracycline containing agar plates. A single colony is picked and used to inoculate the Master Cell Bank (MCB) shake flask culture (LB broth medium containing tetracycline). The cell suspension from the logarithmic growth phase is mixed 1+1 with 40% w/v Glycerol, aliquoted at 1.8 mL into cryogenic vials, sealed in cryogenic tubing, and frozen in the liquid phase of a liquid nitrogen tank.

The Working Cell Bank is generated in the same way as the Master Cell Bank except that the shake flask culture is inoculated with cell suspension from a thawed MCB vial.

Example 2

Fermentation Process for Production of Recombinant Human Interferon Alpha 2B (rhIFNα2B)

The fermentation process is started by growing the strain *E. coli* K-12 W3110 obtainable from the Working Cell Bank as described above in shake flask cultures in Luria Bertani (LB-) medium at 37° C. with the addition of the antibiotic tetracyclin hydrochloride to avoid growth of non-plasmid carrying cells.

The shake flask culture is then used to inoculate the seed culture (=pre-culture) medium (inoculum size=0.4%). The medium for this pre-culture cultivation is based on deionized water containing glucose as a sole carbon source and yeast autolysate as a complex nitrogen source. In addition, anorganic salts like $KH_2PO_4$, $K_2HPO_4$, $(NH_4)_2SO_4$ and $MgSO_4.7H_2O$ are added to the medium. As an antifoam agent polypropylene glycole 2000 (PPG2000) is used. In particular, the pre-culture medium has the following composition:

Pre-Culture Basal Medium:

| Component | Amount |
|---|---|
| De-ionized water (WBI) | 30 l |
| Yeast autolysate, KAT, Ohly | 21.7 g/l |
| Glucose Monohydrate, pure | 25.0 g/l |
| Ammonium Sulfate, p.a. | 1.0 g/l |
| Potassium Phosphate Monobasic, p.a | 1.5 g/l |
| Potassium Phosphate Dibasic, anhydrous, pure | 3.0 g/l |
| Magnesium Sulfate Heptahydrate, p.a. | 0.5 g/l |
| Polypropylene Glycole 2000 | 0.5 m/l |

These media components are sterilized together for 20 minutes at 121° C. After cooling of the basal medium, an aliquot of a 5 g/L sterile stock-solution of the antibiotic Tetracycline Hydrochloride is added to the basal medium (sterilization is performed by filtration (0.22 μm filter)).

Stock-solution Tetracycline Hydrochloride (5 g/L):

| Component | Amount |
|---|---|
| Tetracycline Hydrochloride cryst., Ph.Eur. | 15 mg/l |
| De-ionized water (WBI) | |

The cultivation-time for seed culture is about 16 hours. During cultivation of the seed culture pH-value is controlled to a set-point of 7.0±0.2 with sulfuric acid and sodium hydroxide or concentrated ammonia solution. Concentration of dissolved oxygen is kept at levels higher than 20% of saturation by increasing the stirrer speed. Stirrer speed at the beginning of the cultivation is set to 300 rpm, back-pressure in the vessel to 0.3 bar and aeration rate is controlled to 30 L/min (equivalent to "1 vvm"). Temperature is kept constantly at 37° C. during cultivation. As a transfer criterion of broth to the main stage of the fermentation process, an increase of the dissolved oxygen concentration after consumption of the carbon source is used.

For main culture cultivation a medium based on deionized water, glucose as a carbon source and yeast autolysate as a complex nitrogen source is used. Besides the addition of the anorganic salts $(NH_4)_2SO_4$, $CaCl_2.2H_2O$ and $MgSO_4.7H_2O$, PPG 2000 is used as an antifoam agent. The initial glucose is sterilized separately and added to the sterile rest of the medium. Inoculum size to the main fermenter medium was in a range between 0.75 and 3%. In particular, the main culture medium has the following composition:

Main Culture Basal Medium:

| Component | Amount |
|---|---|
| De-ionized water (WBI) | 60 l |
| Yeast autolysate, KAT, Ohly | 43.5 g/l |
| Ammonium Sulfate, p.a. | 1.0 g/l |
| Calcium Chloride Dihydrate cryst., p.a. | 0.3 g/l |
| Magnesium Sulfate Heptahydrate, p.a. | 1.0 g/l |
| Polypropylene Glycole 2000 | 0.5 ml/l |

These media components are sterilized together for 20 minutes at 121° C. After cooling, an aliquot of a 800 g/L separately heat-sterilized glucose stock-solution is added to the main culture basal medium (sterilization is performed for more than 30 minutes at 120° C.).

Glucose Stock-solution, 800 g/l:

| Component | Amount |
|---|---|
| Glucose Syrup | 12.5 ml/l |
| De-ionized water (WBI) | |

The most important point during this cultivation is the necessity of a complete consumption of the initial glucose present in the medium. This leads to a sharp increase of dissolved oxygen concentration after about 9 hours of growth. By starting glucose feeding before total consumption of the initial glucose, no product formation is observed. Glucose limitation controlled by the feeding of the glucose-solution at a constant rate is therefore very important. The temperature during cultivation is controlled to a constant value of about 28° C. The initial stirrer speed is set to 300 rpm, the aeration rate is controlled to 100 L/min (equivalent to "1 vvm") and the back-pressure in the vessel is set to 0.3 bar. The pH-value is controlled to 7.1±0.3 with sulfuric acid and sodium hydroxide or concentrated ammonia solution. A peak of the pH-value up to 8.0 after consumption of the initially supplied glucose is acceptable.

The concentration of the dissolved oxygen is controlled to values higher than 20% of saturation. Dependent on the oxygen transfer capacity of the bioreactor DO-concentration is kept at levels higher than 20% of saturation, preferably between about 40% and 100% of saturation, by first increasing the stirrer speed to a maximum value. If this is not sufficient, first aeration rate and after that back-pressure is increased, respectively. After a cultivation time between 48 and 192 hours (linear increase of product formation is observed with cultivation time) the culture is harvested and cooled to 15±5° C. and conditioned for downstream processing by the addition of sucrose/EDTA to the cooled broth.

The results of a fermentation batch is analysed based on the Westernblot technique or on HPLC-measurements after laboratory or pilot plant periplasmatic extraction of the product.

Example 3

Cell Disruption and Extraction

A fermentation broth obtained as described above containing host cells comprising the expressed interferon alpha 2B in the periplasmic space is adjusted with sulfuric acid to pH of 5.0±0.1 immediately after the fermentation and cooled down to 4° C.±2° C. The low pH and the low temperature help to inactivate endogenous proteases.

The fermentation broth is adjusted to 10° C. to 20° C., then without any concentration or washing of the cells, solid or liquid sucrose (200 g sucrose/kg fermentation broth) and EDTA (concentration 10 mM) are added and the pH adjusted to 8.0. After a selective one-step cell permeation protocol using osmotic shock (1+3 dilutions) with cooled water, whereby the fermentation broth comprising sucrose and EDTA is poured or pumped into the cooled (temperature about 4° C.) water, the released periplasmic extract is clarified. Polyethyleneimine is added to a final concentration of 0.05% and the pH is adjusted to about 7.5 with acetic acid. After 15 to 45 minutes cell debris and DNA flocculate, leaving a clear crude extract containing interferon which may be subject to centrifugation to improve clarity.

This procedure leads to a clear periplasmic extract comprising the desired interferon alpha 2B in high yield with a purity of >20% with respect to the total protein content. Polyethyleneimine helps to separate the cell debris from the soluble protein extract leading to a very pure interferon solution.

Example 4

Chromatographic Purification of Recombinant Human Interferon α 2B (rhIFNα2B)

4.1 Capture by Cation Exchange Chromatography (CEX)

After pH adjustment to 4.8-5.2 with acetic acid and a filtration step using a 0.3 micron filter, the crude extract of Example 3 is applied to the CEX column (S ceramic HyperD F (Biosepra)). After a washing step with an equilibration buffer (20 mM sodium acetate and 70 mM NaCl at pH 5.0) the interferon is eluted with a step gradient at 175 mM NaCl. The fraction collected is immediately processed by the process step of Example 4.2.

4.2 Anion Exchange (AEX) Chromatography

The fraction from Example 4.1 is adjusted to a pH of 7.3 to 7.7 with sodium hydroxide, diluted and purified with water to a conductivity of 3.5 to 4.5 mS/cm and applied to the AEX column (Q ceramic HyperD F (Biosepra)). After washing, the interferon is eluted with a linear salt gradient (0-300 mM NaCl) at about 150 mM NaCl. Fractions are collected that have a purity of greater than or equal to 90 area % according to IPC reversed-phase HPLC and used directly in the next step (see Example 4.3).

4.3 Hydrophobic Interaction Chromatography (HIC)

The fraction of Example 4.2 is diluted (1:1) with a stock solution of sodium sulphate (0.5% sodium sulphate), adjusted to pH 7.3 to 7.7 with NaOH or HCl and applied to the HIC column (Source 15PHE (Pharmacia). After washing, the interferon fraction of Example 3 is eluted with a linear sodium sulphate concentration (800-0 mM sodium sulphate) at about 400 mM sodium sulphate. The fractions collected that have a purity of greater than or equal to 93 area % and no impurity greater than or equal to 3% according to IPC reversed-phase HPLC are used directly in the next purification step.

4.4 Cation Exchange Chromatography (CEX)

The collected fractions of Example 4 are diluted with water to a final conductivity of 7.5 to 8.5 mS/cm, adjusted to pH 4.3 to 4.7 with 99 to 100% acetic acid and applied to the CEX column (Toyopearl SP-650 S (TosoHaas)). After a washing step, the interferon is eluted in a linear NaCl gradient (0-300 mM NaCl) at about 250 mM NaCl. The fractions are collected that have a purity of greater than or equal to 95 area % and no impurity greater than or equal to 3% according to IPC reversed-phase HPLC and are used directly in the next purification step.

4.5 Size Exclusion Chromatography

The last purification step is a gel filtration step to remove dimers and other aggregates and to perform a buffer exchange for the final formulation. The Superdex 75 pg used in this step shows a good resolution even at a high load volume (5%-15%). The SEC is performed in 25 mM sodium phosphate and 130 mM NaCl+0.3 mM EDTA at a pH of about 7.3 to 7.7.

The fractions with the highest purity (>95% main peak in RP-HPLC and no side peak>3%) are pooled to give the final bulk solution comprising the desired recombinant human interferon α 2B in pure form in a high yield.

---

The invention claimed is:

1. An expression vector comprising a polynucleotide which encodes a heterologous fusion protein containing (i) a single signal sequence polypeptide consisting of the signal sequence of the gac gene of *Pseudomonas diminuta* and (ii) a polypeptide of interest other than gac gene of *Pseudomonas diminuta*, wherein said signal sequence of SEQ ID NO: 2 and said polypeptide of interest are linked so that upon expression of the polynucleotide as a fusion protein in a suitable host cell, the signal sequence is cleaved off the fusion protein and the polypeptide of interest is released into the periplasm of the host cell.

2. The vector according to claim 1, wherein said vector is a plasmid.

3. The vector according to claim 1, wherein said vector is a high copy plasmid.

4. The vector according to claim 1, wherein the polypeptide of interest is interferon alpha 2.

5. The vector according to claim 4, wherein the interferon alpha 2 is selected from the group consisting of interferon alpha 2A and interferon alpha 2B.

6. The vector according to claim 1, wherein said vector further comprises a second polynucleotide comprising the promoter region and the ribosomal binding site of the gac gene of *Pseudomonas diminuta*, wherein the second polynucleotide is operatively linked to the polynucleotide encoding the fusion protein comprising the signal sequence and the polypeptide of interest.

7. The vector according to claim 6, wherein said second polynucleotide comprising the promoter region and the ribosomal binding site comprises the nucleotide sequence.

8. The vector according to claim 7, wherein said second polynucleotide comprising the promoter region and the ribosomal binding site comprises the nucleotide sequence SEQ ID NO: 6.

9. A prokaryotic host cell containing an expression vector which comprises a polynucleotide which encodes a heterologous fusion protein containing (i) a single signal sequence consisting of the signal sequence of the gac gene of *Pseudomonas diminuta* of SEQ ID NO: 2 and (ii) a polypeptide of interest, other than the gac gene of *Pseudomonas diminuta*, wherein said signal sequence and said polypeptide of interest are linked, so that upon expression of the polynucleotide as a fusion protein in a suitable host cell, the signal sequence is cleaved off the fusion protein and the polypeptide of interest is released into the periplasm of the host cell, wherein the host cell is stably transformed by the expression vector.

10. The host cell according to claim 9, wherein said vector is a plasmid.

11. The host cell according to claim 9, wherein said vector is a high copy plasmid.

12. The vector according to claim 9, wherein the polypeptide of interest is interferon alpha 2.

13. The vector according to claim 9, wherein the interferon alpha 2 is selected from the group consisting of interferon alpha 2A and interferon alpha 2B.

14. The host cell according to claim 9, wherein said vector further comprises a second polynucleotide comprising the promoter region and the ribosomal binding site of the gac gene of *Pseudomonas diminuta*, wherein the second polynucleotide is operatively linked to the polynucleotide encoding the fusion protein comprising the signal sequence and the polypeptide of interest, wherein the promoter region promotes expression of both the first and the second polynucleotide.

15. The host cell according to claim 14, wherein said second polynucleotide comprising the promoter region and the ribosomal binding site comprises the nucleotide sequence.

16. The host cell according to claim 14, wherein said second polynucleotide comprising the promoter region and the ribosomal binding site comprises the nucleotide sequence SEQ ID NO: 6.

17. The host cell according to claim 9, wherein said host cell is an *E. coli* cell.

18. A process for production of a polypeptide of interest, comprising:
  (i) providing a prokaryotic host cell transformed with an expression vector which is compatible with the host cell, said vector comprising a polynucleotide which encodes a heterologous fusion protein which comprises (a) a single signal sequence consisting of the signal sequence of the gac gene of *Pseudomonas diminuta* of SEQ ID NO: 2 and (b) a polypeptide of interest, other than the gac gene of *Pseudomonas diminuta*, wherein said signal sequence and said polypeptide of interest are linked so that upon expression of the polynucleotide as a fusion protein in a suitable host cell, the signal sequence is cleaved off the fusion protein and the polypeptide of interest is released into the periplasm of the host cell;
  (ii) culturing the prokaryotic host cell under conditions which cause expression of the polynucleotide as a fusion protein, whereby upon formation of the fusion protein the signal sequence is cleaved off the fusion protein and the polypeptide of interest is released into the periplasm of the host cell; and
  (iii) isolating the polypeptide of interest from the host cell.

19. The process according to claim 18, wherein said vector is a plasmid.

20. The process according to claim 18, wherein said vector is a high copy plasmid.

21. The vector according to claim 18, wherein the polypeptide of interest is interferon alpha 2.

22. The vector according to claim 21, wherein the interferon alpha 2 is selected from the group consisting of interferon alpha 2A and interferon alpha 2B.

23. The process according to claim 18, wherein said vector further comprises a second polynucleotide comprising the promoter region and the ribosomal binding site of the gac gene of *Pseudomonas diminuta*, wherein the second polynucleotide is operatively linked to the polynucleotide encoding the fusion protein comprising the signal sequence and the polypeptide of interest, wherein the promoter region promotes expression of both the first and the second polynucleotide.

24. The process according to claim 23, wherein said second polynucleotide comprising the promoter region and the ribosomal binding site comprises the nucleotide sequence SEQ ID NO: 5.

25. The process according to claim 23, wherein said second polynucleotide comprising the promoter region and the ribosomal binding site comprises the nucleotide sequence (SEQ ID NO: 6)

```
5'-TCTAGACCAACAACATCTTCAACGTCTACCCGACCAAGATTCAGGAG
CCGTCGGCCGACCTGGGCAATGGGATGTACAGCGGGCTTGCGCCGTTCGG
CTTCACCGGCGGATCCTGGTTCGTACGCGCCGCCTACAAGTGGTGATCTA
GGGGAACGTTCCGGGGGCGTCGCTGCAACGGCGTCTCCGGATCTGGGTGA
GAGGGGAAATCC-3'.
```

26. The process according to claim 18, wherein said host cell is an *E. coli* cell.

27. The process according to claim 18, said culturing being performed as a multi-stage fermentation process comprising a shake-flask step, optionally a pre-culture step, and a main-culture step.

28. The process according to claim 27, wherein said culturing of the procaryotic host cell in the main culture step is performed in a culture medium comprising a substrate for more than about 90% of the cultivation time at a substrate concentration lower than the saturation constant of the substrate, accompanied by high levels of dissolved oxygen concentration, and further accompanied by a steadily decreasing specific growth rate of the bacterial host cells, the process being performed at a temperature which is lower than the optimum temperature for growth of the host cell.

29. The process according to claim 28, wherein the concentration of dissolved oxygen in the main culture step is from about 40% up to about 100% of saturation.

30. The process according to claim 28, wherein the steadily decreasing growth rate in the main culture step is from about 2 h$^{-1}$ to about 0.001 h$^{-1}$.

31. The process according to claim 28, wherein the temperature in the main culture step is between about 22° C. and about 35° C.

32. The process according to claim 31, wherein the temperature in the main culture step is between about 25° C. and about 31° C.

33. The process according to claim 32, wherein the temperature in the main culture step is about 28° C.

34. The process according to claim 28, wherein said process is performed at a pH value in the range of about 6.7 to about 7.3 in the pre-culture step and/or the main-culture step.

35. The process as claimed in claim 28, wherein the substrate is a carbohydrate or glycerol.

36. The process according to claim 35, wherein the carbohydrate is glucose.

37. The process according to claim 28, wherein the host cell is an *E. coli* cell.

38. A prokaryotic host cell transformed with an expression vector which is compatible with the host cell, said vector comprising:
  a) a first polynucleotide encoding a fusion protein which comprises i) a single signal sequence consisting of the signal sequence of a gac gene of *Pseudomonas diminuta* of SEQ ID NO: 6 and ii) a polypeptide of interest selected from the group consisting of human interferon alpha 2A and human interferon alpha 2B, wherein said signal sequence and said polypeptide of interest are linked so that upon expression of the first polynucleotide as a fusion protein in a suitable host cell, the signal sequence is cleaved off the fusion protein and the polypeptide of interest is released into the periplasm of the host cell, wherein the host cell is an *E. coli* cell; and b) a second polynucleotide comprising a promoter region and a ribosomal binding site of the gac gene of *Pseudomonas diminuta*, wherein the second polynucleotide is operatively linked to the first polynucleotide encoding the fusion protein comprising the signal sequence and the polypeptide of interest, wherein the promoter region promotes expression of both the first and the second polynucleotide.

39. A process for production of a polypeptide of interest, comprising:

(i) providing a prokaryotic host cell transformed with an expression vector which is compatible with the host cell, said vector comprising:

a polynucleotide encoding a fusion protein which comprises i) a single signal sequence, wherein the signal sequence consists of the signal sequence of gac gene of *Pseudomonas diminuta*; of SEQ ID NO:2 a promoter region of gac gene of *Pseudomonas diminuta*; and a ribosomal binding site of gac gene of *Pseudomonas diminuta*; and ii) a polypeptide of interest selected from the group consisting of human interferon alpha 2A and human interferon alpha 2B, wherein said signal sequence and said polypeptide of interest are linked so that upon expression of the first polynucleotide as a fusion protein in a suitable host cell, the signal sequence, promoter region and ribosomal binding site are cleaved off the fusion protein, and the polypeptide of interest is released into the periplasm of the host cell, wherein the promoter region promotes expression of both the first and the second polynucleotide, and wherein the host cell is an *E. coli* cell; and (ii) culturing the prokaryotic host cell under conditions which cause expression of the first polynucleotide whereby upon formation of the fusion protein the signal sequence is cleaved off the fusion protein and the polypeptide of interest is released into the periplasm of the host cell; and (iii) isolating the polypeptide of interest from the host cell.

* * * * *